United States Patent
Walker et al.

(10) Patent No.: US 9,994,315 B2
(45) Date of Patent: Jun. 12, 2018

(54) UNMANNED AERIAL VEHICLES IN MEDICAL APPLICATIONS

(71) Applicant: PHYSIO-CONTROL, INC., Redmond, WA (US)

(72) Inventors: Robert G. Walker, Redmond, WA (US); Mitchell Smith, Redmond, WA (US); Kristina Furlan, Redmond, WA (US); John Daynes, Redmond, WA (US); Michael Arbuck, Redmond, WA (US); Alex Esibov, Redmond, WA (US); Melissa Pochop-Miller, Redmond, WA (US); Dennis Skelton, Redmond, WA (US)

(73) Assignee: Physio-Control, Inc., Redmond, WA (US)

( * ) Notice: Subject to any disclaimer, the term of this patent is extended or adjusted under 35 U.S.C. 154(b) by 0 days. days.

(21) Appl. No.: 15/213,377

(22) Filed: Jul. 18, 2016

(65) Prior Publication Data

US 2017/0137124 A1 May 18, 2017

Related U.S. Application Data

(60) Provisional application No. 62/193,077, filed on Jul. 16, 2015.

(51) Int. Cl.
*B64C 39/02* (2006.01)
*A61N 1/39* (2006.01)
(Continued)

(52) U.S. Cl.
CPC .......... *B64C 39/024* (2013.01); *A61B 5/0022* (2013.01); *A61B 5/0205* (2013.01);
(Continued)

(58) Field of Classification Search
CPC . B64C 39/024; B64C 2201/12; A61B 5/0022; A61B 5/0205; A61B 5/0255;
(Continued)

(56) References Cited

U.S. PATENT DOCUMENTS

| 8,948,935 B1 * | 2/2015 | Peeters | B64C 39/024 701/3 |
| 8,983,682 B1 * | 3/2015 | Peeters | B64C 39/024 244/190 |

(Continued)

OTHER PUBLICATIONS

Di Bin, Zhou Rui, Wu Jiang and Chen Shaodong, "Distributed Coordinated Task Allocation for Heterogeneous UAVs Based on Capacities", 2013 10th IEEE International Conference on Control and Automation (ICCA), Hangzhou, China, Jun. 12-14, 2013 (Year: 2013).*

*Primary Examiner* — Krishnan Ramesh
(74) *Attorney, Agent, or Firm* — Lane Powell PC

(57) ABSTRACT

Systems and methods for the use of unmanned aerial vehicles (UAVs) in medical emergencies are disclosed herein. The systems and methods include receiving at a first UAV an indication of a medical emergency and coordinating with a second UAV based on the second UAV's capabilities. The first UAV determines if the capabilities of the second UAV complement the capabilities of the first UAV based on the indicated medical emergency. The disclosed systems and methods deploy both the first and second UAVs to the medical emergency if the capabilities of the second UAV complement those of the first UAV.

3 Claims, 5 Drawing Sheets

(51) Int. Cl.

| | |
|---|---|
| *A61B 5/0255* | (2006.01) |
| *A61B 5/08* | (2006.01) |
| *A61B 5/00* | (2006.01) |
| *A61B 5/0205* | (2006.01) |
| *G06F 19/00* | (2018.01) |
| *G08B 25/10* | (2006.01) |
| *G08B 21/02* | (2006.01) |
| *G08B 25/08* | (2006.01) |
| *A61B 5/021* | (2006.01) |
| *A61B 5/026* | (2006.01) |
| *A61B 5/0402* | (2006.01) |

(52) U.S. Cl.
CPC .............. *A61B 5/0255* (2013.01); *A61B 5/08* (2013.01); *A61B 5/082* (2013.01); *A61N 1/39* (2013.01); *G06F 19/3418* (2013.01); *G08B 21/02* (2013.01); *G08B 25/08* (2013.01); *G08B 25/10* (2013.01); *A61B 5/021* (2013.01); *A61B 5/026* (2013.01); *A61B 5/0402* (2013.01); *A61B 5/747* (2013.01); *A61B 2505/01* (2013.01); *B64C 2201/12* (2013.01)

(58) Field of Classification Search
CPC ........... A61B 5/08; A61B 5/082; A61B 5/021; A61B 5/026; A61B 5/0402; A61B 5/747; G06F 19/3418; G08B 25/10

USPC ........................................................... 701/3
See application file for complete search history.

(56) References Cited

U.S. PATENT DOCUMENTS

| | | | |
|---|---|---|---|
| 9,051,043 B1* | 6/2015 | Peeters | B64C 19/00 |
| 9,307,383 B1* | 4/2016 | Patrick | H04W 4/22 |
| 9,589,448 B1* | 3/2017 | Schneider | G08B 25/016 |
| 9,760,072 B2* | 9/2017 | Hall | G05B 15/02 |
| 9,848,459 B2* | 12/2017 | Darrow | H04W 84/18 |
| 9,849,979 B2* | 12/2017 | Peeters | B64C 39/024 |
| 2007/0129855 A1* | 6/2007 | Coulmeau | G08G 5/0039 |
| | | | 701/3 |
| 2011/0130636 A1* | 6/2011 | Daniel | G08B 25/016 |
| | | | 600/301 |
| 2014/0316243 A1* | 10/2014 | Niedermeyer | A61B 5/7264 |
| | | | 600/408 |
| 2015/0148988 A1* | 5/2015 | Fleck | G05D 1/0011 |
| | | | 701/2 |
| 2016/0042637 A1* | 2/2016 | Cahill | G08B 25/10 |
| | | | 701/3 |
| 2017/0092109 A1* | 3/2017 | Trundle | B60L 11/1824 |
| 2017/0144757 A1* | 5/2017 | Hall | B64C 39/024 |
| 2017/0154536 A1* | 6/2017 | Kreiner | G08G 5/0043 |
| 2017/0295609 A1* | 10/2017 | Darrow | H04W 84/18 |

\* cited by examiner

400 A computer program product

402 A signal bearing medium 404 at least one of machine readable non-transitory medium having stored therein instructions that, when executed by one or more processors, operatively enable a unmanned ariel vehicle control module to:

receive an indication of a medical emergency;

coordinate with a second UAV to travel to a location of the medical emergency, the coordinating including an indication of a capabilities of the second UAV;

determine if the capabilities of the second UAV complements a capabilities of the UAV based, at least in part, on the received indication of the medical emergency; and if it is determined that the capabilities of the second UAV complements the capabilities of the UAV, deploy the UAV and the second UAV towards the location of the medical emergency.

| 406 a computer-readable medium | 408 a recordable medium | 410 a communications medium |

Figure 4

UNMANNED AERIAL VEHICLES IN MEDICAL APPLICATIONS

RELATED APPLICATION

This application claims benefit of priority to U.S. Provisional Patent Application Ser. No. 62/193,077 filed on Jul. 16, 2015, entitled METHOD AND SYSTEMS FO USING UAVS IN MEDICAL APPLICATIONS, which is incorporated herein by reference in its entirety.

BACKGROUND

Unless otherwise indicated herein, the approaches described in this section are not prior art to the claims in this application and are not admitted to be prior art by inclusion in this section.

An unmanned aerial vehicle (UAV) may be used in variety of applications. In some examples, a UAV may be used to view an area from an aerial vantage point. In another example, a UAV may be used to deliver a package. However, use of a UAV may not include actual useful interaction capabilities and/or features.

BRIEF DESCRIPTION OF THE DRAWINGS

Subject matter is particularly pointed out and distinctly claimed in the concluding portion of the specification. The foregoing and other features of the present disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings.

In the drawings:

FIG. 4 illustrates an example computer program product 400, arranged in accordance with at least some embodiments described herein.

DETAILED DESCRIPTION

Figure 1:
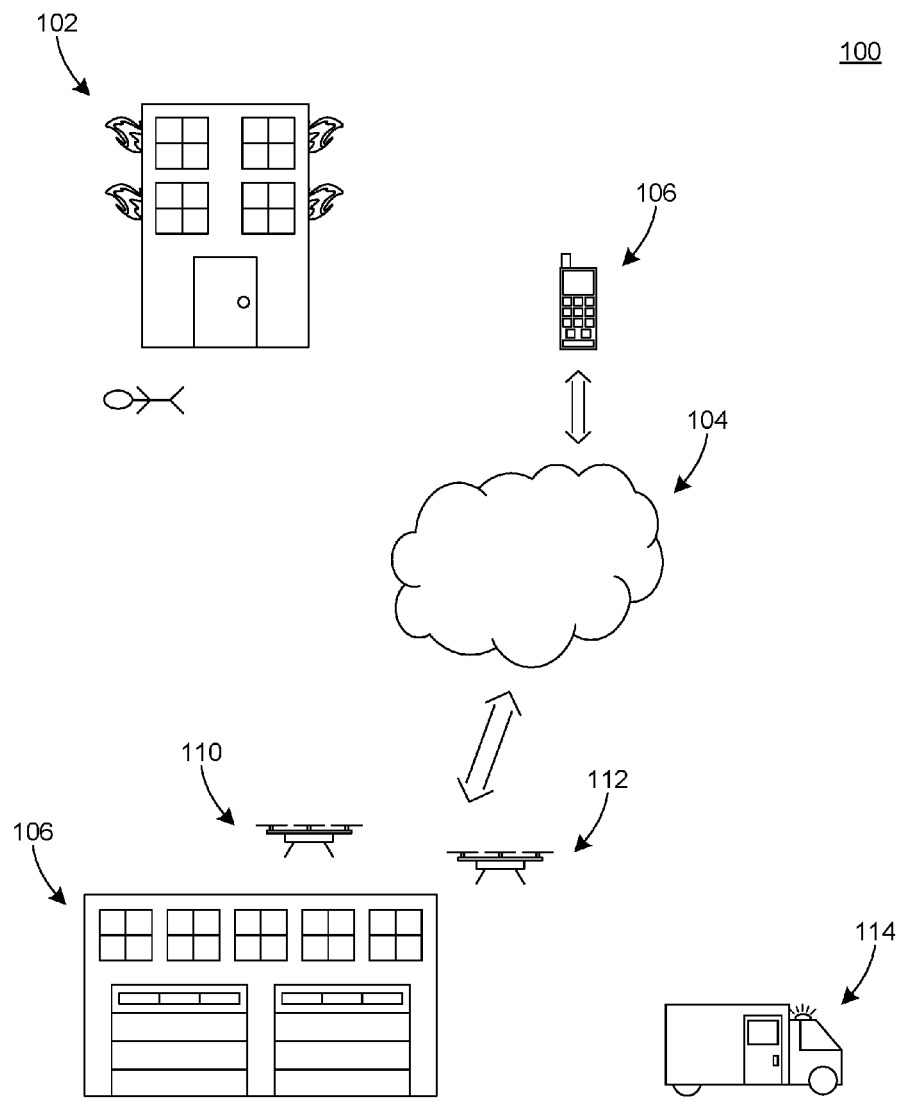
FIG. 1 illustrates a block diagram of an example system in accordance with various embodiments.

The following description sets forth various examples along with specific details to provide a thorough understanding of claimed subject matter. It will be understood by those skilled in the art, however, that claimed subject matter may be practiced without some or more of the specific details disclosed herein. Further, in some circumstances, well-known methods, procedures, systems, components and/or circuits have not been described in detail in order to avoid unnecessarily obscuring claimed subject matter.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the Figures, can be arranged, substituted, combined, and designed in a wide variety of different configurations, all of which are explicitly contemplated and make part of this disclosure.

This disclosure is drawn, inter alia, to methods, apparatus, and systems related to utilization of unmanned aerial vehicles (UAVs) in medical applications.

As applications of UAVs become wide spread and varied, the capabilities of UAVs have become more sophisticated. As the capabilities of the UAVs become more sophisticated, interactions with the UAVs may become more complex and/or sophisticated as well. Additionally, some applications may include the utilization of more than a single UAV. Coordination and/or control of multiple UAVs may be complicated, especially if utilizing the capabilities of each of the multiple UAVs.

In order to better understand the present disclosure, a couple of non-limiting scenarios illustrating utilization of the present disclosure may be described. In a non-limiting scenario, a UAV may include capabilities such as, but not limited to, medical capabilities. The medical capabilities may include emergency medical capabilities such as, but not limited to, medical equipment capabilities. For example, the UAV may be capable of transporting an automated external defibrillator (AED), or the UAV may have integrated defibrillator capabilities. In addition to medical equipment capabilities, the UAV may include interface capabilities. For example, the UAV may include a display to facilitate interaction with a person. The interaction may include, but not limited to, facilitating communication of various health related indicators of a patient, facilitating communication of instructions for the treatment of the patient, facilitating communication with a remote medical personnel, etc.

In one non-limiting scenario, a first responder entity such as, but not limited to, a hospital may receive an indication of a medical emergency. The hospital may have a UAV having at least some of the capabilities described herein. The UAV may be deployed to a location of the medical emergency. In this non-limiting scenario, the medical emergency may be that a patient is having a heart condition, where the patient's hear needs to be defibrillated. In one example, the UAV may be configured to carry an AED to the location of the medical emergency. In another example, the UAV may be configured to include an AED as part of its system. In yet another example, the UAV may be configured to have as a detachable component an AED.

Continuing with the non-limiting scenario of the AED being deployed from the hospital, the AED may arrive at the location of the medical emergency having the necessary medical equipment and/or information to treat the patient. In one example, the UAV may arrive before emergency personnel. In this situation, the UAV may be configured to communicate with people around the medical emergency. For example, when the UAV arrives at the location, the UAV be configured to assess the health of the patient (i.e., determine the health status of the patient). Accordingly, the UAV may be configured to facilitate communication with a bystander. The UAV may instruct the bystander on how to treat the patient (e.g., defibrillate the patient). The UAV may instruct the bystander to remove the AED and/or AED components from itself and attach the appropriate components to the patient. Once the AED components have been attached, the UAV may instruct the bystander on the activation and use of the AED on the patient.

In one example, the UAV may be configured to monitor the patient's health (e.g., via the AED components). For example, the monitoring may include monitoring such as, but not limited to, a patient's electrocardiogram (i.e., ECG or EKG), and so forth. The patient's ECG information may be received and stored for later retrieval back at the hospital. Alternatively, the patient's ECG information may be transmitted to a wireless network and received at the hospital in real time. In another example, the UAV may be configured to monitor a patient's health by measuring breathing (e.g., capnography functionality). The UAV may be configured to monitor the concentration of $CO_2$ at the end of each exhaled breath by the patient. The concentration of $CO_2$ at the end of each exhaled breath may be known as end-tidal carbon dioxide ($ETCO_2$). The health monitoring device may provide information related to the cardiac output, pulmonary blood flow (i.e., perfusion) as the $CO_2$ and/or fractional $CO_2$ may be transported by the circulatory system to the right side of the heart and then pumped into the lungs by the right ventricle, alveolar ventilation at the lungs, respiratory issues, metabolism, etc. Accordingly, the UAV having capnography functionality may facilitate monitoring of the patient's health.

Continuing with the non-limiting example scenario, by the time an emergency personnel arrives at the location of the medical emergency, the patient may have been treated. Additionally, as previously mentioned, the UAV may be configured to include a wide variety of applications. For example, once the emergency personnel arrives at the location of the medical emergency, the UAV may be configured to include various medical supplies and/or components such as, but not limited to, various medication, cardiopulmonary resuscitation related components (e.g., machines), respirator/ventilator related components, medicine delivery system components (e.g., intravenous (IV) delivery systems), continuous positive airway pressure (CPAP) components (e.g., CPAP machines), etc., and accordingly, the claimed subject matter is not limited in these respects. These supplies and/or components may be configured to be removable and/or replaceable and may include various power supplies to provide power (e.g., battery, solar, generator, etc.) Along these lines, the UAV may include various ports and/or connectors configured to provide power to the various components, and additionally, the various ports and/or connectors may be configured to provide data communication capabilities.

In another non-limiting scenario, a first responder entity such as, but not limited to, a fire station may receive an indication of an emergency, which may include medical emergency. For example, the fire station may receive an indication of a building fire with fire victims. The fire station may have several UAVs having at least some of the capabilities described herein. Before being deployed, the UAVs may be coordinated to provide the optimum response for the emergency situation. For example, one UAV may be configured to include various medical related supplies and/or components for the treatment of the fire victims, while another UAV may be configured to include various fire fighting related supplies and/or components (e.g., forward looking infrared imaging components to help facilitate detection of hot spots, audio components such as loud speakers for bystander control, information gathering component such as an interface for interacting with fire victims and/or bystanders, etc.). In addition to and/or alternatively to, all of the UAVs may be configured to include all of these supplies and/or components. However, for this non-limiting example scenario, the two UAVs may be configured to include different supplies and/or components to complement each other.

Continuing with this non-limiting example scenario, the first UAV configured to include medical related supplies and/or components may determine and select the second UAV configured to include fire related supplies and/or components to complement its configuration. Once this determination is made for the appropriate supplies/components for the emergency situation, the two UAVs may be deployed to the location of the fire. Once the UAVs arrive at the location, the first UAV may provide the medical related services to the fire victims, while the second UAV may assess the location for further dangers (e.g., hotspots) and may provide crowd control for any bystanders. Once the emergency personnel arrives at the location, both of the UAVs may provide support, supplies, and/or components for the emergency personnel (e.g., the second UAV may be configured to include a handheld fire extinguisher). The second UAV may provide the handheld fire extinguisher to a bystander and provide instructions on its use. Alternatively, the handheld fire extinguisher may be provided to emergency personnel (e.g., a firefighter).

Because of the speed, with which UAVs may arrive at an emergency destination, the UAVs may be considered to be the first responders. As described in the present disclosure, the UAVs may be coordinated to be emergency personnel at a location of an emergency.

Continuing with the non-limiting example scenario of more than one UAV responding to an emergency, a fleet of UAVs may be configured to coordinate with each other to provide supplies and/or components for a wide range of situations. In one example, a fleet of UAVs may be configured to coordinate with each other to provide supplies and/or components for a disaster natural and/or human made. The coordination of the UAVs may include coordination of the various configurations of the UAVs to provide the appropriate assistance (e.g., medical, law enforcement, fire fighting, imaging such as infrared, radar, etc., and so forth).

Even though the present disclosure may be described with respect to emergency applications, it will be appreciated that the claimed subject matter may be applicable to wide range of applications, which may utilize first responders. Accordingly, the claimed subject matter is not limited in these respects.

Turning now to FIG. 1, where FIG. 1 illustrates a block diagram of an example system in accordance with various embodiments. In FIG. 1, a system 100 may include a location of an emergency 102, a network 104, and a first responder entity 106. Additionally, the system 100 may include a communication device 108, a first UAV, a second UAV 112, and a first responder vehicle 114, and a patient 116. For ease of understanding the system 100, the various components may be referred to in terms more commonly associated with emergency situations. Accordingly, in a non-limiting example, the system 100 may be a fire emergency situation. The location of the emergency 102 may be referred to a building fire, the network 104 may be referred to as a wireless network, the first responder entity 106 may be referred to as a fire station, the communication device 108 may be referred to as a mobile phone, the first UAV 110 may be referred to as a medical drone, the second UAV 112 may be referred to as a firefighting drone, and the first responder vehicle 114 may be referred to as a fire truck.

In FIG. 1, the mobile phone 108 may be used to make a call to emergency responders regarding the building fire 102. The call may be made to an emergency system such as 911 via the wireless network 104. An indication of the building fire 102 may be received at the fire station 106 via the wireless network 104. In one example, the medical drone 110 may receive the indication of the building fire. The indication may include an indication of a medical emergency (e.g., medical needs of the patient 116). Because the received indication of an emergency may include a fire emergency in addition to the medical emergency, the medical drone 110 may coordinate with the firefighting drone 112. The coordination may include determining the capabilities of the firefighting drone 112 (e.g., that the second UAV 112 may be configured to include supplies and/or components related to firefighting). If the medical drone 110 determines that the capabilities of the firefighting drone 112 complements its capabilities, the medical drone 110 and the firefighting drone 112 may be deployed to the building fire 102. However, if the medical drone 110 determines that the firefighting drone 112 capabilities did not complement its capabilities (e.g., the second UAV may be configured to include supplies and/or components for land surveying, for animal control, law enforcement, flood assistance, etc.), medical drone 110 may search other UAVs (not shown) to find the one that may compliment its capabilities. In addition to and/or alternatively, the medical drone may coordinate with a UAV configured to include supplies and/or components to facilitate other medical needs (e.g., one medical drone may be configured to include supplies and/or components for AED applications, while a second medical drone may be configured to include supplies and/or components for CPAP applications). In addition to and/or alternatively, the emergency may require more than one firefighting drone 112 and/or more than one medical drone 110. The coordination to complement the capabilities may be based, at least in part, on the type and nature of the emergency.

As previously described, the fire truck 114 may arrive at the building fire 102 before the medical drone 110 and the firefighter drone 112. However, once the first responders arrive at the building fire 102, the first responders may utilize any of the supplies and/or components made available by the medical drone 110 and the firefighter drone 112.

In FIG. 1, the mobile phone 108 may be any type of communication method such as, but not limited to, wired communication method, wireless communication method, an automated system (e.g., an alarm system, fire detection system, medical emergency alert system, etc.), and so forth. Accordingly, the claimed subject matter is not limited in these respects.

Before moving on, it should be appreciated that the first UAV 110 and the second UAV 112 may communicate with each other in a variety of manners such as, but not limited to, WiFi, Bluetooth, Ethernet, near field communication, etc. Accordingly, the claimed subject matter is not limited in these respects.

Additionally, the first responder vehicle 114 may be a wide variety of first responder vehicles such as, but not limited to, a boat, a helicopter, an airplane, a train, etc. Accordingly, the claimed subject matter is not limited in these respects.

Figure 2:
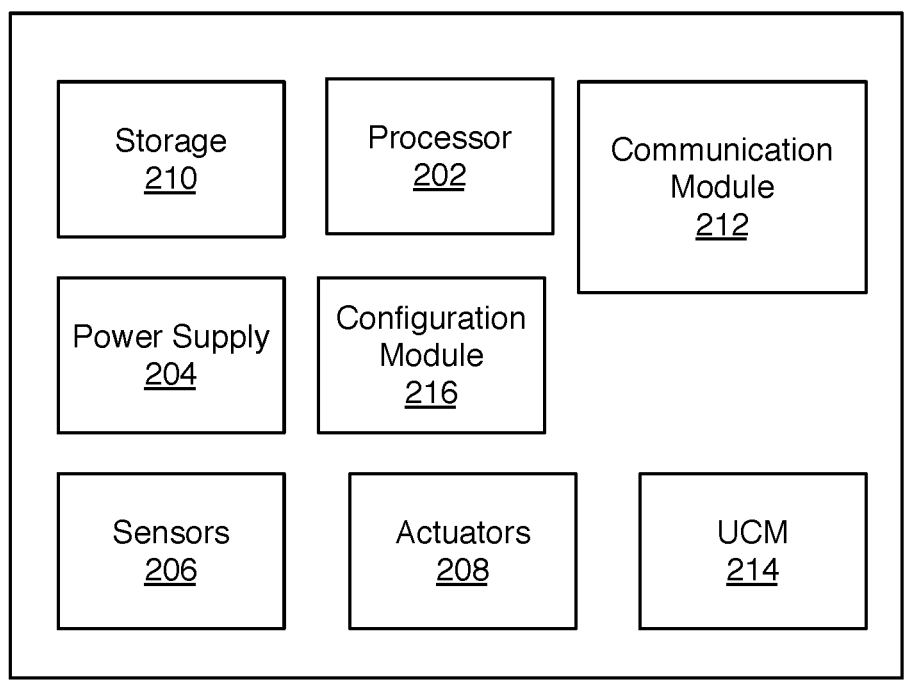
FIG. 2 illustrates (FIG. 2) a block diagram of a UAV, in accordance with various embodiments.

FIG. 2 illustrates (FIG. 2) a block diagram of a UAV, in accordance with various embodiments. In FIG. 2, a UAV 200 may include a processor 202, an power supply 204, various sensors 206, various actuators 208, storage medium 210, a communication module 212, a UAV control module (UCM) 214, and configuration module 216. In FIG. 2, the UCM 214 may be communicatively coupled to the processor 202 and may be configured to receive an indication of an emergency, such as, but not limited to an medical emergency. The UCM 214 of the UAV 200 may coordinate with a second UAV (shown in FIG. 1) to travel to a location of the emergency, where the coordination may include an indication of capabilities of the second UAV. Additionally, the UCM 214 may determine if the capabilities of the second UAV complements capabilities of the UAV 200, where the capabilities of the UAV 200 may be found in the configuration module 216. The configuration module may include the wide variety of configurations to include supplies and/or components for various applications as previously described. These configurations may be stored in the storage medium 206. If it is determined that the capabilities of the second UAV complements the capabilities of the UAV 200, the UCM 214 may be configured to deploy the UAV 200 and the second UAV towards the location of the emergency.

Briefly turning back to FIG. 1, in the fire emergency situation 100, the medical drone 110 may coordinate with the firefighter drone 112 via a wireless communication method. Together, the medical drone 110 and the firefighter drone 112 may deploy towards the building fire 102.

Figure 3:
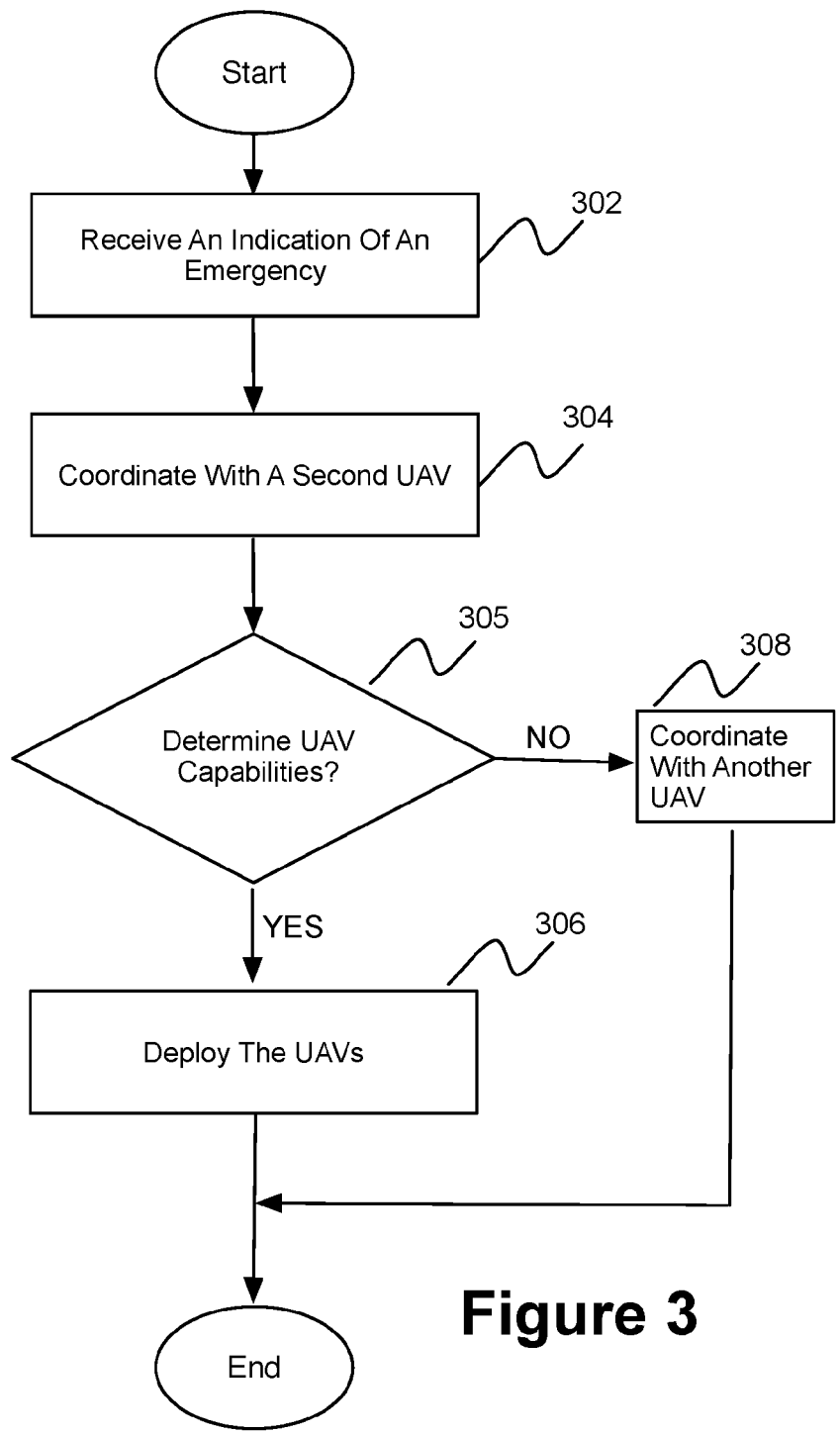
FIG. 3 illustrates an operational flow for use of UAVs in emergency applications, arranged in accordance with at least some embodiments described herein.

FIG. 3 illustrates an operational flow for use of UAVs in emergency applications, arranged in accordance with at least some embodiments described herein. In some portions of the description, illustrative implementations of the method are described with reference to the elements of the components described with respect to FIGS. 1 and 2. However, the described embodiments are not limited to these depictions. More specifically, some elements depicted in FIGS. 1 and 2 may be omitted from some implementations of the methods detailed herein. Furthermore, other elements not depicted in FIGS. 1 and 2 may be used to implement example methods detailed herein.

Additionally, FIG. 3 employs block diagrams to illustrate the example methods detailed therein. These block diagrams may set out various functional block or actions that may be described as processing steps, functional operations, events and/or acts, etc., and may be performed by hardware, software, and/or firmware. Numerous alternatives to the functional blocks detailed may be practiced in various implementations. For example, intervening actions not shown in the figures and/or additional actions not shown in the figures may be employed and/or some of the actions shown in one figure may be operated using techniques discussed with respect to another figure. Additionally, in some examples, the actions shown in these figures may be operated using parallel processing techniques. The above described, and other not described, rearrangements, substitutions, changes, modifications, etc., may be made without departing from the scope of the claimed subject matter.

In some examples, operational flow 300 may be employed as part of a UAV. As previously described, the UAV may include a UCM and a signal bearing medium.

Beginning at block 302 ("Receive An Indication Of An Emergency"), the UCM 214 may receive at a first UAV an indication of a medical emergency.

Continuing from block 302 to 304 ("Coordinate With A Second UAV"), the UCM 412 may coordinate with a second UAV to travel to a location of the medical emergency. The coordinating may include an indication of capabilities of the second UAV. The UCM 214 may determine at the first UAV if the capabilities of the second UAV compliments capabilities of the first UAV, at decision block 305 ("Determining UAV Capabilities"). Determining whether the capabilities of the UAVs compliment each other may be based, at least in part, on the received indication of the medical emergency.

Continuing from decision block 305 to block 306 ("Deploy The UAVs"), if it is determined that the capabilities of the second UAV compliments the capabilities of the first UAV, the first UAV and the second UAV may be deployed towards the location of the medical emergency.

However, if it is determined that the capabilities of the second UAV do not compliment the capabilities of the first UAV, the first UAV may coordinate with another UAV at block 308 ("Coordinate With Another UAV").

In general, the operational flow described with respect to FIG. 3 and elsewhere herein in may be implemented as a computer program product, executable on any suitable computing system, or the like. For example, a computer program product for facilitating use of a UAV for medical applications. Example computer program products may be described with respect to FIG. 4 and elsewhere herein.

FIG. 4 illustrates an example computer program product 400, arranged in accordance with at least some embodiments described herein. Computer program product 400 may include machine readable non-transitory medium having stored therein instructions that, when executed, cause the machine to utilize a UAV for emergency applications, according to the processes and methods discussed herein. Computer program product 400 may include a signal bearing medium 402. Signal bearing medium 402 may include one or more machine-readable instructions 404, which, when executed by one or more processors, may operatively enable a computing device to provide the functionality described herein. In various examples, the devices discussed herein may use some or all of the machine-readable instructions.

In some examples, the machine readable instructions 404 may include instructions that, when executed, cause the machine to receive at a first UAV an indication of an emergency such as a medical emergency. In some examples, the machine readable instructions 404 may include instructions that, when executed, cause the machine to coordinate with a second UAV to travel to a location of the medical emergency, where the coordinating may include an indication of a capabilities of the second UAV. In some examples, the machine readable instructions 404 may include instructions that, when executed, cause the machine to determine at the first UAV if the capabilities of the second UAV complements a capabilities of the first UAV based, at least in part, on the received indication of the medical emergency. In some examples, the machine readable instructions 404 may include instructions that, when executed, cause the machine to if it is determined that the capabilities of the second UAV complements the capabilities of the first UAV, deploy the first UAV and the second UAV towards the location of the medical emergency.

In some implementations, signal bearing medium 402 may encompass a computer-readable medium 406, such as, but not limited to, a hard disk drive, a Compact Disc (CD), a Digital Versatile Disk (DVD), a digital tape, memory, etc. In some implementations, the signal bearing medium 402 may encompass a recordable medium such as, but not limited to, memory, read/write (R/W) CDs, R/W DVDs, etc. In some implementations, the signal bearing medium 402 may encompass a communications medium such as, but not limited to, a digital and/or an analog communication medium (e.g., a fiber optic cable, a waveguide, a wired communication link, a wireless communication link, etc.). In some examples, the signal bearing medium 402 may encompass a machine readable non-transitory medium.

In general, the methods described with respect to FIG. 4 and elsewhere herein may be implemented in any suitable computing system. Example systems may be described with respect to FIG. 5 and elsewhere herein. In general, the system may be configured to facilitate utilization a UAV in emergency applications.

Figure 5:
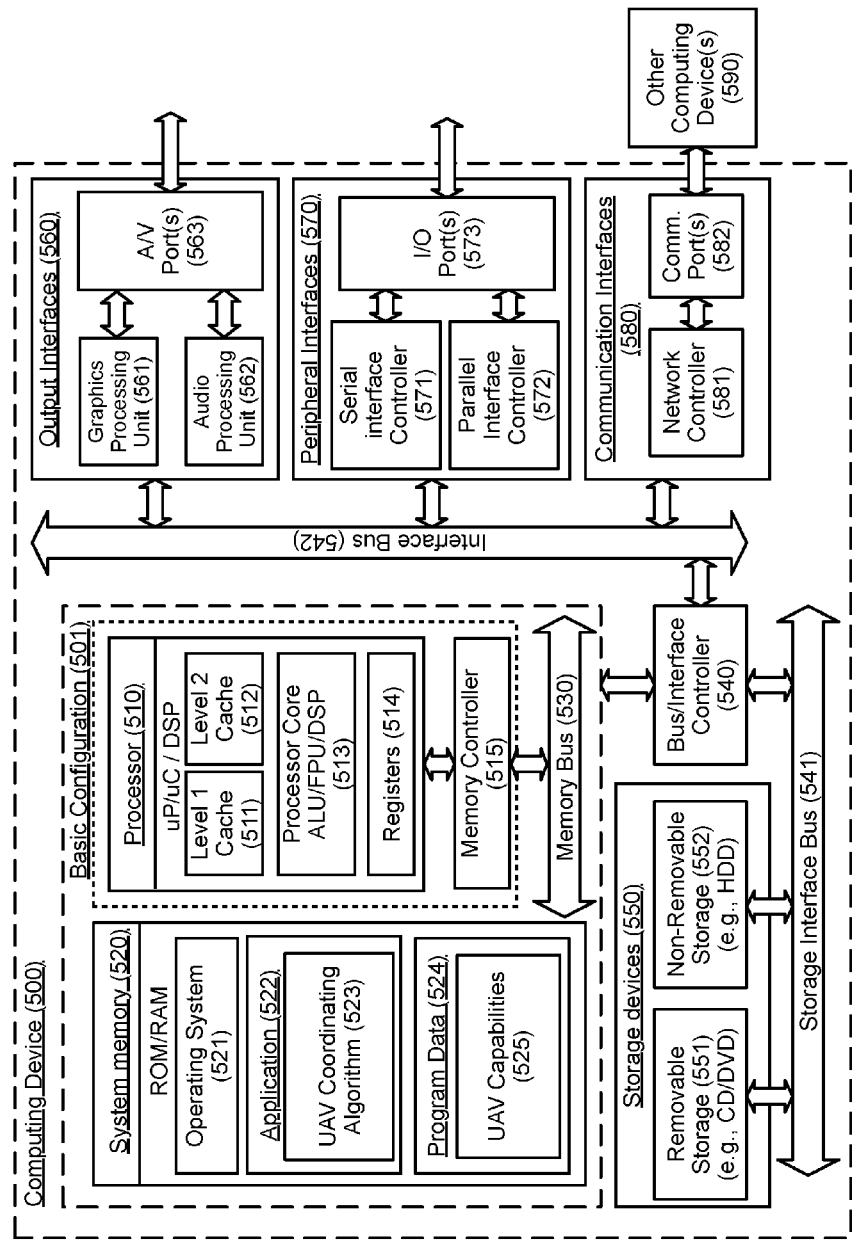
FIG. 5 is a block diagram illustrating an example computing device, such as might be embodied by a person skilled in the art, which is arranged in accordance with at least some embodiments of the present disclosure.

FIG. 5 is a block diagram illustrating an example computing device 500, such as might be embodied by a person skilled in the art, which is arranged in accordance with at least some embodiments of the present disclosure. In one example configuration 501, computing device 500 may include one or more processors 510 and system memory 520. A memory bus 530 may be used for communicating between the processor 510 and the system memory 520.

Depending on the desired configuration, processor 510 may be of any type including but not limited to a microprocessor (µP), a microcontroller (µC), a digital signal processor (DSP), or any combination thereof. Processor 510 may include one or more levels of caching, such as a level one cache 511 and a level two cache 512, a processor core 513, and registers 514. The processor core 513 may include an arithmetic logic unit (ALU), a floating point unit (FPU), a digital signal processing core (DSP Core), or any combination thereof. A memory controller 515 may also be used with the processor 510, or in some implementations the memory controller 515 may be an internal part of the processor 510.

Depending on the desired configuration, the system memory 520 may be of any type including but not limited to volatile memory (such as RAM), non-volatile memory (such as ROM, flash memory, etc.) or any combination thereof. System memory 520 may include an operating system 521, one or more applications 522, and program data 524. Application 522 may include UAV coordinating algorithm 523 that is arranged to perform the functions as described herein including the functional blocks and/or actions described. Program Data 524 may include, among many information described, UAV capabilities 525 for use with UAV coordinating algorithm 523. In some example embodiments, application 522 may be arranged to operate with program data 524 on an operating system 521 such that implementations of a UAV may be provided as described herein. For example, apparatus described in the present disclosure may comprise all or a portion of computing device 500 and be capable of performing all or a portion of application 522 such that implementations of a UAV may be provided as described herein. This described basic configuration is illustrated in FIG. 5 by those components within dashed line 501.

Computing device 500 may have additional features or functionality, and additional interfaces to facilitate communications between the basic configuration 501 and any required devices and interfaces. For example, a bus/interface controller 540 may be used to facilitate communications between the basic configuration 501 and one or more data storage devices 550 via a storage interface bus 541. The data storage devices 550 may be removable storage devices 551, non-removable storage devices 552, or a combination thereof. Examples of removable storage and non-removable storage devices include magnetic disk devices such as flexible disk drives and hard-disk drives (HDD), optical disk drives such as compact disk (CD) drives or digital versatile disk (DVD) drives, solid state drives (SSD), and tape drives to name a few. Example computer storage media may include volatile and nonvolatile, removable and non-removable media implemented in any method or technology for storage of information, such as computer readable instructions, data structures, program modules, or other data.

System memory 520, removable storage 551 and non-removable storage 552 are all examples of computer storage media. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which may be used to store the desired information and which may be accessed by computing device 500. Any such computer storage media may be part of device 500.

Computing device 500 may also include an interface bus 542 for facilitating communication from various interface devices (e.g., output interfaces, peripheral interfaces, and communication interfaces) to the basic configuration 501 via the bus/interface controller 540. Example output interfaces 560 may include a graphics processing unit 561 and an audio processing unit 562, which may be configured to communicate to various external devices such as a display or speakers via one or more A/V ports 563. Example peripheral interfaces 560 may include a serial interface controller 571 or a parallel interface controller 572, which may be configured to communicate with external devices such as input devices (e.g., keyboard, mouse, pen, voice input device, touch input device, etc.) or other peripheral devices (e.g., printer, scanner, etc.) via one or more I/O ports 573. An example communication interface 580 includes a network controller 581, which may be arranged to facilitate communications with one or more other computing devices 590 over a network communication via one or more communication ports 582. A communication connection is one example of a communication media. Communication media may typically be embodied by computer readable instructions, data structures, program modules, or other data in a modulated data signal, such as a carrier wave or other transport mechanism, and may include any information delivery media. A "modulated data signal" may be a signal that has one or more of its characteristics set or changed in such a manner as to encode information in the signal. By way of example, and not limitation, communication media may include wired media such as a wired network or direct-wired connection, and wireless media such as acoustic, radio frequency (RF), infrared (IR) and other wireless media. The term computer readable media as used herein may include both storage media and communication media.

Computing device 500 may be implemented as a portion of a small-form factor portable (or mobile) electronic device such as a cell phone, a personal data assistant (PDA), a personal media player device, a wireless web-watch device, a personal headset device, an application specific device, or a hybrid device that includes any of the above functions. Computing device 500 may also be implemented as a personal computer including both laptop computer and non-laptop computer configurations. In addition, computing device 500 may be implemented as part of a wireless base station or other wireless system or device.

Some portions of the foregoing detailed description are presented in terms of algorithms or symbolic representations of operations on data bits or binary digital signals stored within a computing system memory, such as a computer memory. These algorithmic descriptions or representations are examples of techniques used by those of ordinary skill in the data processing arts to convey the substance of their work to others skilled in the art. An algorithm is here, and generally, is considered to be a self-consistent sequence of operations or similar processing leading to a desired result. In this context, operations or processing involve physical manipulation of physical quantities. Typically, although not necessarily, such quantities may take the form of electrical or magnetic signals capable of being stored, transferred, combined, compared or otherwise manipulated. It has proven convenient at times, principally for reasons of common usage, to refer to such signals as bits, data, values, elements, symbols, characters, terms, numbers, numerals or the like. It should be understood, however, that all of these and similar terms are to be associated with appropriate physical quantities and are merely convenient labels. Unless specifically stated otherwise, as apparent from the following discussion, it is appreciated that throughout this specification discussions utilizing terms such as "processing," "computing," "calculating," "determining" or the like refer to actions or processes of a computing device, that manipulates or transforms data represented as physical electronic or magnetic quantities within memories, registers, or other information storage devices, transmission devices, or display devices of the computing device.

Claimed subject matter is not limited in scope to the particular implementations described herein. For example, some implementations may be in hardware, such as employed to operate on a device or combination of devices, for example, whereas other implementations may be in software and/or firmware. Likewise, although claimed subject matter is not limited in scope in this respect, some implementations may include one or more articles, such as a signal bearing medium, a storage medium and/or storage media. This storage media, such as CD-ROMs, computer disks, flash memory, or the like, for example, may have instructions stored thereon, that, when executed by a computing device, such as a computing system, computing platform, or other system, for example, may result in execution of a processor in accordance with claimed subject matter, such as one of the implementations previously described, for example. As one possibility, a computing device may include one or more processing units or processors, one or more input/output devices, such as a display, a keyboard and/or a mouse, and one or more memories, such as static random access memory, dynamic random access memory, flash memory, and/or a hard drive.

There is little distinction left between hardware and software implementations of aspects of systems; the use of hardware or software is generally (but not always, in that in certain contexts the choice between hardware and software can become significant) a design choice representing cost vs. efficiency tradeoffs. There are various vehicles by which processes and/or systems and/or other technologies described herein can be affected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; if flexibility is paramount, the implementer may opt for a mainly software implementation; or, yet again alternatively, the implementer may opt for some combination of hardware, software, and/or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a flexible disk, a hard disk drive (HDD), a Compact Disc (CD), a Digital Versatile Disk (DVD), a digital tape, a computer memory, etc.; and a transmission type medium such as a digital and/or an analog communication medium (e.g., a fiber optic cable, a waveguide, a wired communications link, a wireless communication link, etc.).

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms.

For example, the phrase "A or B" will be understood to include the possibilities of "A" or "B" or "A and B."

Reference in the specification to "an implementation," "one implementation," "some implementations," or "other implementations" may mean that a particular feature, structure, or characteristic described in connection with one or more implementations may be included in at least some implementations, but not necessarily in all implementations. The various appearances of "an implementation," "one implementation," or "some implementations" in the preceding description are not necessarily all referring to the same implementations.

While certain exemplary techniques have been described and shown herein using various methods and systems, it should be understood by those skilled in the art that various other modifications may be made, and equivalents may be substituted, without departing from claimed subject matter. Additionally, many modifications may be made to adapt a particular situation to the teachings of claimed subject matter without departing from the central concept described herein. Therefore, it is intended that claimed subject matter not be limited to the particular examples disclosed, but that such claimed subject matter also may include all implementations falling within the scope of the appended claims, and equivalents thereof.

What is claimed:

1. A method of using an unmanned aerial vehicles (UAVs) in medical applications, the method comprising:
    at a first UAV having at least a first capability, receiving an indication of a medical emergency;
    at the first UAV, coordinating with a second UAV to travel to a location of the medical emergency, the coordinating including an indication of at least a second capability of the second UAV;
    at the first UAV, determining if the at least a second capability of the second UAV complements the at least a first capability of the first UAV based, at least in part, on the received indication of the medical emergency; and
    if it is determined that the at least a second capability of the second UAV complements the at least a first capability of the first UAV, deploying the first UAV and the second UAV towards the location of the medical emergency.

2. The method of claim 1 further comprising:
    if it is determined that the at least a second capability of the second UAV does not complement the at least a first capability of the first UAV, coordinating with a third UAV to travel to the location of the medical emergency, the coordinating including an indication of at least a third capability of the third UAV.

3. An unmanned aerial vehicle (UAV) comprising:
    a processor;
    a storage medium communicatively coupled to the processor; and
    a UAV control module (UCM) communicatively coupled to the processor, the UCM configured to:
        receive an indication of a medical emergency;
        coordinate with a second UAV to travel to a location of the medical emergency, the coordinating including an indication of at least a second capability of the second UAV;
    determine if the at least a second capability of the second UAV complements at least a first capability of the UAV based, at least in part, on the received indication of the medical emergency; and
    if it is determined that the at least a second capability of the second UAV complements the at least a first capability of the UAV, deploy the UAV and the second UAV towards the location of the medical emergency.

* * * * *